(12) United States Patent
Larsen

(10) Patent No.: US 9,433,690 B1
(45) Date of Patent: Sep. 6, 2016

(54) RADIOPHARMACEUTICAL SOLUTIONS WITH ADVANTAGEOUS PROPERTIES

(71) Applicant: Sciencons AS, Oslo (NO)

(72) Inventor: Roy Hartvig Larsen, Oslo (NO)

(73) Assignee: SCIENCONS AS, Oslo (NO)

( * ) Notice: Subject to any disclaimer, the term of this patent is extended or adjusted under 35 U.S.C. 154(b) by 0 days.

(21) Appl. No.: 14/632,849

(22) Filed: Feb. 26, 2015

(51) Int. Cl.
*A61K 51/00* (2006.01)
*A61M 36/14* (2006.01)
*A61K 51/10* (2006.01)

(52) U.S. Cl.
CPC ........... *A61K 51/1069* (2013.01); *A61K 51/00* (2013.01); *A61K 51/1018* (2013.01); *A61K 51/1045* (2013.01); *A61K 51/1051* (2013.01)

(58) Field of Classification Search
CPC .. A61K 2123/00; A61K 51/00; A61K 51/04; A61K 51/0474; A61K 51/0476; A61K 51/0478; A61K 51/0482; A61K 51/0485; A61K 51/088; A61K 51/1045; A61K 51/1051; A61K 51/1018; A61K 51/1069; C07F 13/005
USPC .............. 424/1.11, 1.49, 1.65, 1.69, 9.1, 9.2, 424/178.1, 179.1; 514/1, 1.1, 19.2, 19.3, 514/19.5, 19.6, 19.8, 19.9, 19.4; 534/10, 12
See application file for complete search history.

(56) References Cited

U.S. PATENT DOCUMENTS 6,592,843 B2 * 7/2003 Larsen et al. ................. 424/1.21
8,535,639 B2 * 9/2013 Brechbiel et al. ........... 424/1.11
2007/0224115 A1 * 9/2007 Barr et al. ................... 424/1.11
2009/0311174 A1 * 12/2009 Allen ........................... 424/1.49
2014/0348745 A1 * 11/2014 Larsen et al. ............... 424/1.49

OTHER PUBLICATIONS

Yong et al, Dalton Trans., 2011, vol. 40, No. 23, pp. 6068-6076.*
Golub et al., Science, Oct. 15, 1999, pp. 531-537.*
Jaggi, Jaspreet Singh et al., "Efforts to Control the Errant Products of a Targeted In vivo Generator" Cancer Res, Jun. 1, 2005, pp. 4888-4895, vol. 65, No. 11.
Jones, Shaun B. et al., "Evaluation of Dithiol Chelating Agents as Potential Adjuvants for Anti-IL-2 Receptor Lead or Bismuth Alpha Radioimmunotherapy" Nuclear Medicine & Biology, 1996, pp. 105-113, vol. 23.
Nilsson, Sten et al., "First Clinical Experience with α-Emitting Radium-223 in the Treatment of Skeletal Metastases" Clin Cancer Res, Jun. 15, 2005, pp. 4451-4459, vol. 11, No. 12.

* cited by examiner

*Primary Examiner* — D L Jones
(74) *Attorney, Agent, or Firm* — Knobbe, Martens, Olson & Bear, LLP

(57) ABSTRACT

Methods and solutions are describes whereby radiopharmaceutical radium-224 solutions are added complex for scavenging daughter nuclide, which may enhance the overall targeting and reduces uptake of daughter nuclide in normal tissues and cells. This is accomplished without reducing the bone targeting ability of radium. The methods and solutions are convenient to use since the complexation of daughter nuclide can be done in situ in a ready to use radiopharmaceutical solution or, depending on the activity concentration, in a simple kit format by mixing two solutions and store the mixture for typically 1 minute to a few hours before administration to a patient. The use of targeted chelate scavengers for $^{224}$Ra daughter nuclide opens up the possibility for using $^{224}$Ra based solutions for medical treatments.

8 Claims, 10 Drawing Sheets

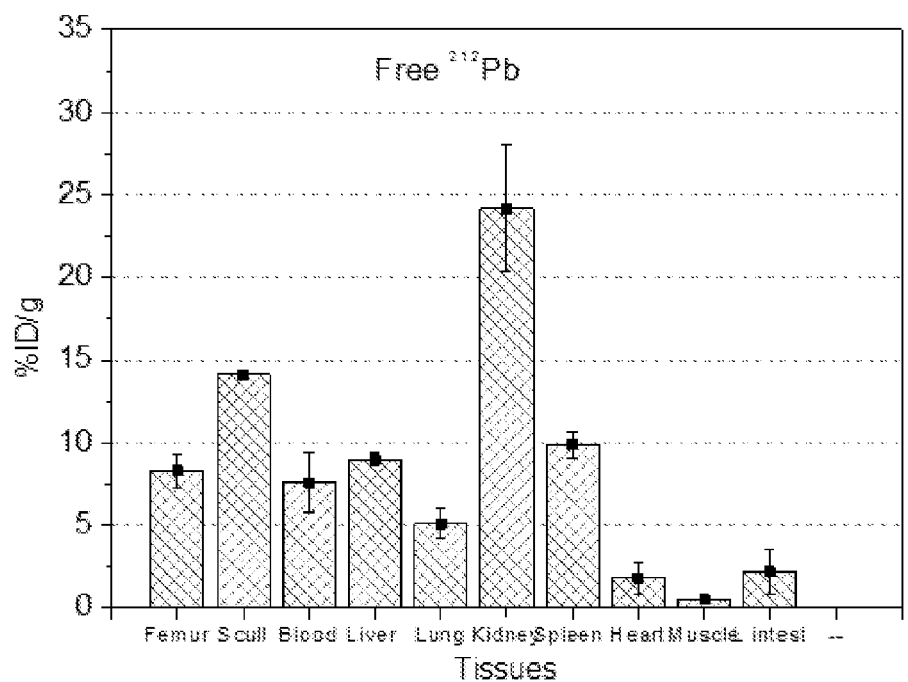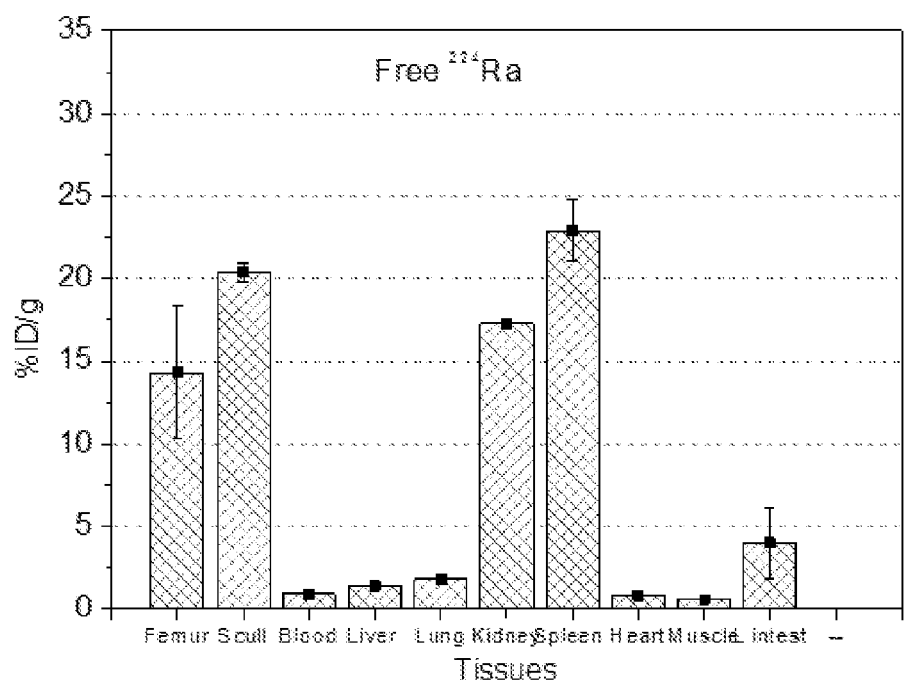
Fig. 3A

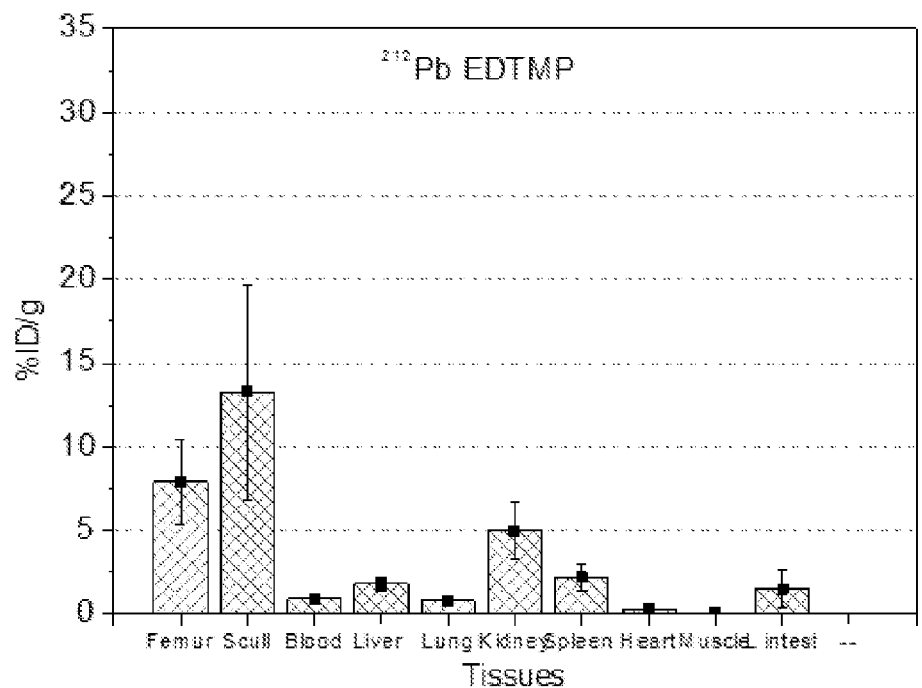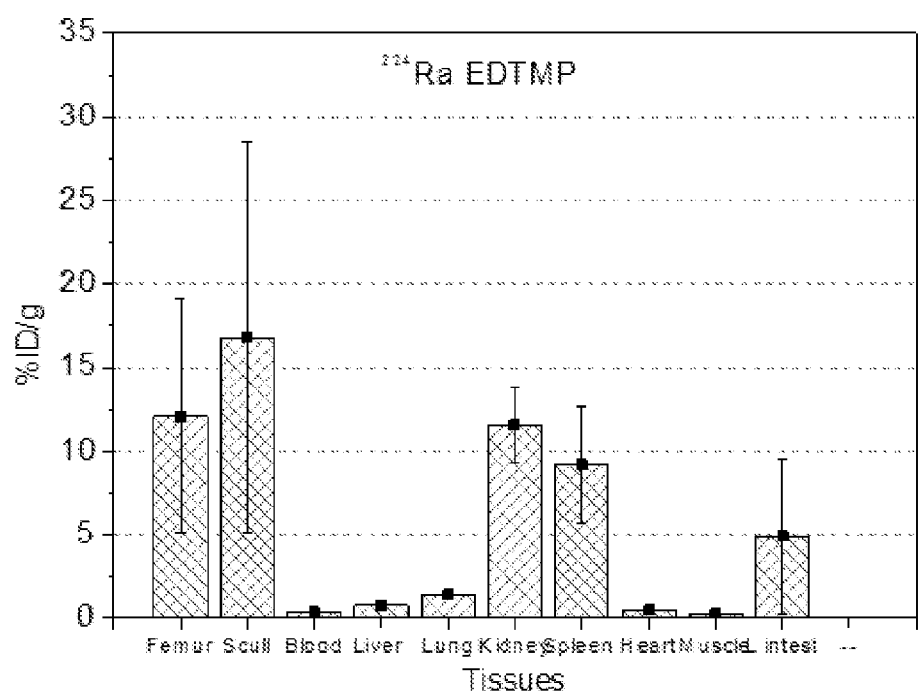
Fig. 3B

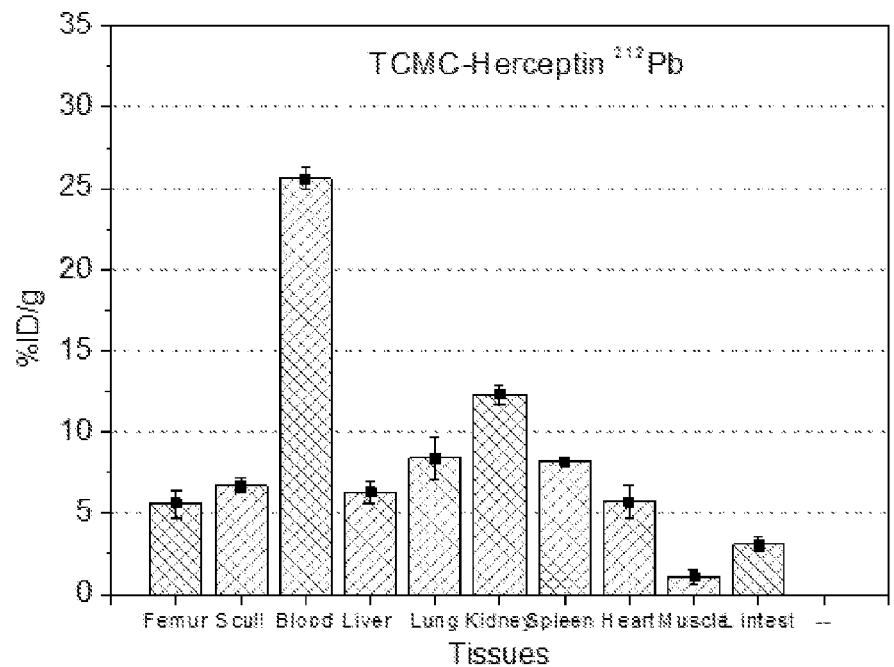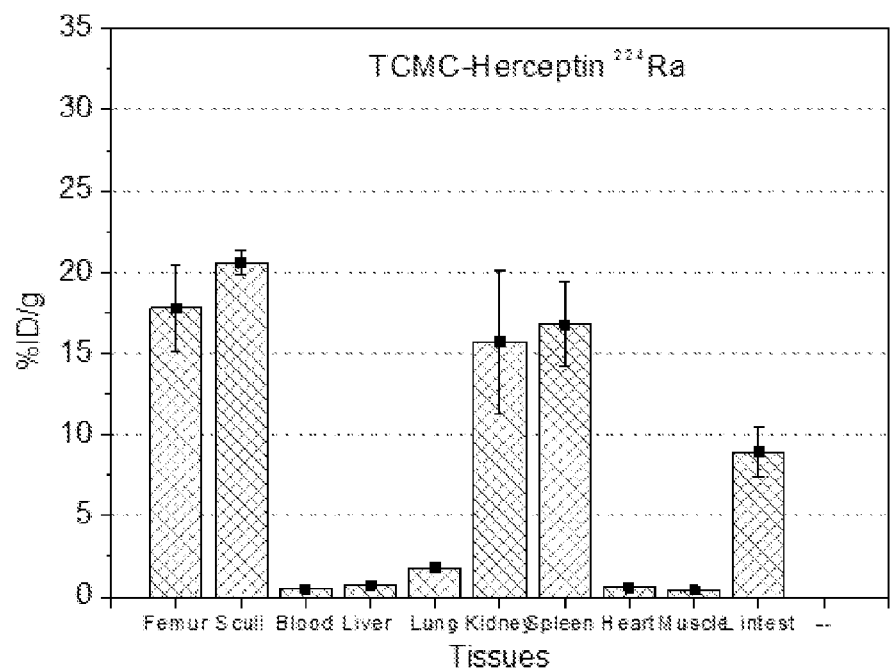
Fig. 3C

| Radionuclide (half life) | Alphas and betas (mean energy in MeV) | X-rays and gammas Energy and % abundance |
|---|---|---|
| $^{224}$Ra (3.6 days) | α 5.6 | 241 keV, 4.1% |
| $^{220}$Rn (55.6 s) | α 6.3 | |
| $^{216}$Po (145 ms) | α 6.8 | |
| $^{212}$Pb (10.6 h) | β 0.1 | 75 keV, 10.3% <br> 77 keV, 17.1% <br> 87 keV, 6.0% <br> 90 keV, 1.5% <br> 239 keV, 43.6% <br> 300 keV, 3.3% |
| $^{212}$Bi (10.6 h) | α 6.1 × 0.36 (2.2 MeV effective¹) <br> β 0.7 × 0.64 (0.4 MeV effective) | 727 keV, 6.7% (4.3% effective) |
| $^{212}$Po (299 ns) (64% branch) | α 8.8 (5.6 effective) | |
| $^{208}$Tl (3.1 min) (36% branch) | β 0.6 (0.2 MeV effective) | 75 keV, 3.4% (1.2% effective) <br> 511 keV, 22.6% (8.1% effective) <br> 583 keV, 85.0% (30.6% effective) <br> 860 keV, 12.5% (4.5% effective) <br> 2615 keV, 99.8% (35.9% effective) |

Fig. 4

| Time point | 0 h | 2 h | 6 h | 12 h | 24 h | 36 h | 2 days | 3 days | 1 week |
|---|---|---|---|---|---|---|---|---|---|
| $^{224}$Ra (MBq) | 10 | 9.8 | 9.5 | 9.1 | 8.3 | 7.5 | 6.8 | 5.7 | 2.7 |
| $^{212}$Pb (MBq) | 0 | 1.2 | 3.1 | 5.1 | 7.0 | 7.5 | 7.3 | 6.3 | 3.0 |
| Activity ratio $^{212}$Pb vs. $^{224}$Ra | 0 | 0.12 | 0.33 | 0.56 | 0.84 | 1.0 | 1.1 | 1.1 | 1.1 |

Fig. 5

| Applied sample | $^{224}$Ra | $^{224}$Ra + FB | $^{224}$Ra + EDTMP | $^{224}$Ra + DOTMP | $^{224}$Ra + DOTMP + FB |
|---|---|---|---|---|---|
| Upper half of TLC-strip | | > 97% of $^{212}$Pb | > 95% of $^{212}$Pb | | |
| Lower half of TLC-strip | > 97% of $^{212}$Pb | | | >97% of $^{212}$Pb | > 77% of $^{212}$Pb |

Fig. 6A

| Applied sample | $^{224}Ra$ + TCMC-mAb + FB | $^{224}Ra$ + TCMC-mAb + EDTMP | $^{224}Ra$ + DOTA-mAb + FB |
|---|---|---|---|
| Upper half of TLC-strip | | | |
| Lower half of TLC-strip | > 92% of $^{212}Pb$ | > 92% of $^{212}Pb$ | > 94% of $^{212}Pb$ |

Fig. 6B

|  | Bone vs. blood | Bone vs. kidney |
|---|---|---|
| $^{212}$Pb non-complexed | 1.1 | 0.36 |
| $^{212}$Pb-EDTMP | 9.5 | 1.57 |
| $^{212}$Pb-TCMC-Herceptin | 0.22 | 0.46 |

Fig. 7

RADIOPHARMACEUTICAL SOLUTIONS WITH ADVANTAGEOUS PROPERTIES

BACKGROUND OF THE INVENTION

1. Field of the Invention

The present invention relates to a radiopharmaceutical solution comprising $^{224}$Ra and a complex capable of scavenging $^{212}$Pb and/or $^{212}$Bi. This solution can be used for medical purposes, including treatment of cancer. Further aspects of the invention relates to kits and methods for providing specific solutions.

2. Description of the Related Art

Targeted alpha particle radionuclide therapy holds promise as therapeutic modality against malignant and non-malignant diseases. Alpha-emitting radionuclides are highly cytotoxic and the alpha particles produced are of high linear energy, which is delivering a high amount of ionization over a short range, causing destruction of DNA by a high degree of irreparable double strand breaks.

Thus, it is important when using alpha emitting radionuclides that they do reach the target and are not released from the targeting compound and that they do not produce longer lived daughter nuclides that diffuse away from the mother nuclide, since this can cause toxicity in remote tissues.

There are relatively few alpha emitters considered for medical applications. It is a challenge in the field to find a radionuclide with appropriate half life, decay properties, chemical properties and daughter products that are suitable for development of medical treatments.

Radium was very important for the development of radio-chemistry sciences and was also used by the pioneers of radio-oncology to treat cancer with brachytherapy (, that is radiation emitting needles or seeds placed within or nearby tumors. Initially $^{226}$Ra with a half life ($t_{1/2}$) of 1600 years was used. Later on $^{224}$Ra ($t_{1/2}$=3.66 days), as dissolved radium chloride injectates, was used for several decades in Germany for the palliative treatment of ankylosing spondylitis (AS) because of the natural bone-seeking property of this, the heaviest of the alkaline earth elements.

Although reintroduced after the development of improved purification methods for a brief period about year 2000, its use was finally abandoned partly due to fear of late effects and the appearance of new treatment options for AS. Therefore $^{224}$Ra is not in use as a radiopharmaceutical today and is not considered among the plausible candidates for alpha therapy by leading experts in the field.

There is, however, research going on using $^{224}$Ra loaded wires for local intratumoral brachytherapy/radon diffusion therapy but they are not using aqueous $^{224}$Ra solutions for therapy.

Recently, another radium isotope, $^{223}$Ra, in the form of a dissolved salt injectate, has been granted market authorization as a treatment against skeletal metastases from castration resistant prostate cancer.

When comparing $^{223}$Ra ($t_{1/2}$=11.4 days) with $^{224}$Ra ($t_{1/2}$=3.6 days) both have, in principal, relevant half-lives for radiopharmaceutical uses allowing centralized production and shipment to the end user and both have three alpha emitting progenies in their decay chains and the series are producing a similar amount of alpha particles (FIGS. 1 and 2) with total alpha energy of about 26-28 MeV for the respective chains.

When comparing the decay chains, $^{223}$Ra progenies of the Rn, Pb and Bi elements have significant shorter half lives reducing the problem of daughter nuclide uptake in non-target cells and tissues. These differences are particularly important for the lead progenies as these can accumulate in hematopoietic cells and tissues and in kidneys, respectively. In the $^{223}$Ra series $^{211}$Pb ($t_{1/2}$=36.1 min) would cause much less normal tissue exposure compared with $^{212}$Pb ($t_{1/2}$=10.6 hours) from the $^{224}$Ra series. Unless $^{224}$Ra is purified from $^{212}$Pb, short before injection, $^{223}$Ra would have significantly less normal tissue exposure from progenies. Such purification is impractical since it would require laborious procedures to be performed at the hospital where the product is being used or that the production and use is being geographically restricted. That is why the time frame for use of $^{224}$Ra that was previously supplied by Altmann Terapie, Salzgitter, Germany, for AS, was of only 6 hours. It could be used 3 hours before or three hours after the calibration time point. Probably to a significant extent because of this short product shelf life (in addition to increased competition with the new drugs for AS) and the thereby logistics and supply constraint the product has been discontinued.

As of currently, there is no use of $^{224}$Ra solution for injection to patients. Instead, there is in development ion exchanger based $^{224}$Ra generators for the extraction of $^{212}$Pb for the use of $^{212}$Pb in radioimmunotherapy. Lead-212 is itself a beta-emitter but decays to the alpha-emitter $^{212}$Bi and is therefore considered suitable as an in vivo generator for alpha particle therapy.

Thus, currently $^{224}$Ra is considered merely as a generator nuclide for the medically useful $^{212}$Pb. Because of the relatively short half life of $^{212}$Pb it is expected to be best suited in treatment against compartmental disease where the radioimmunoconjugate is injected directly into the region, e.g., intraperitoneal (i.p.) cavity where a high concentration of product may target malignant ascites and micrometastases within the cavity. The half life of 10.6 hours of $^{212}$Pb may be of benefit as only low amount leaks out from the i.p. cavity before the radioactivity has decayed.

When considering radium for therapy against bone diseases, it should be kept in a cationic state since this will ensure that that radium, as the so called "volume-seeker" it is, will be built into the bone minerals causing retention of the daughter nuclides. This is particularly important with $^{224}$Ra since some of the daughter nuclides, in particular $^{212}$Pb, have substantial half-lives allowing trans-organ redistribution if let free in physiological liquids like blood, saliva or lymphatic liquid. Table 1 (FIG. 4) lists the main radiation of the decay chain of $^{224}$Ra.

A monograph about the use of $^{224}$Ra in ankylosing spondylitis were developed by the German health authorities about 10 years ago when Altmann Terapie (Salzgitter, Germany) made an effort to re-introduce $^{224}$Ra solution as a treatment against ankylosing spondylitis based on a patented production method yielding a highly purified product.

In the decay chain of $^{224}$Ra the daughter product $^{212}$Pb ($t_{1/2}$=10.6 hours) is produced. It has a different biodistribution compared to the $^{224}$Ra mother nuclide when co-injected in patients. This causes less initial activity in the target tissues and more activity in the non-target tissues like blood cells, in particular hematopoietic cells and tissues, and bone marrow and kidneys. The number of $^{212}$Pb atoms compared with $^{224}$Ra in a product in radioactive equilibrium is less than 14%. But because $^{224}$Ra rapidly transfer from blood to the skeleton or is excreted and $^{212}$Pb is substantially retained in hematopoietic cells and tissues, the toxicological impact of $^{212}$Bi is important. The only way to solve this problem by current knowledge in the field would be to use $^{224}$Ra short time after purification as suggested, that is, before a significant in-growth of $^{212}$Pb has taken place.

The use of scavenger for daughter products in experimental radiopharmaceutical research has been described: Jones et al (1996) studied oral administration over several days of the non-targeted dithiol chelating agents 2,3-dimercapto-1-propanesulfonic acid (DMPS) and meso-2,3-dimercaptosuccinic acid (DMSA) to improve the clearance of $^{206}$Bi from kidneys in mice and found improved kidney clearance with DMPS. Their aim was to use oral chelate as potential adjuvants to reduce or prevent radiotoxicity in anti-interleukin-2 receptor (IL-2R) $^{212}$Pb or $^{212}$Bi alpha-radioimmunotherapy. Jaggi et al., (2005) used oral chelation therapy to reduce renal accumulation of $^{213}$Bi produced from $^{225}$Ac. Their goal was to increase excretion of the undesired daughter product. They did not add the chelator to the radiopharmaceutical but merely describe its use as oral medication in the drinking water before and after injection of radiopharmaceutical.

In terms of bone therapy, $^{223}$Ra is considered more appropriate than $^{224}$Ra because $^{223}$Ra have daughter nuclides with much shorter half-lives and thus, less problem of relocalization. Radium-223 has recently been approved for the therapy of patients with hormone refractory skeletal metastases from prostate cancer.

Dissolved $^{224}$Ra salt has previously been tested in cancer therapy but was abandoned because of unfavorable properties and ineffectiveness. It was stated that because of the short half life of $^{224}$Ra and its injected daughters, the soft tissue(s) are irradiated. In other words in the case of $^{224}$Ra the half life of the daughters, in particular $^{212}$Pb, are relatively long compared to the mother nuclides and more soft tissue exposure occurs. Therefore it is known in the field that $^{224}$Ra has unfavorable daughter nuclide restricting its use in radiopharmaceutical solutions. Also, in recent review by senior experts in the field, $^{224}$Ra was not listed among the candidate radionuclides considered for alpha particle emitter radiopharmaceutical therapy.

The concept of circulating tumor cells (CTC) has lately received considerable attention as CTC may play a critical role in the development of tumor metastases. It is known that cancers that produce skeletal metastases like e.g., prostate-, breast-, lung- and multiple myeloma cancers may have a few viable circulating cancer cells in the blood which may have been shed from the primary or metastatic tumors. This means that even if the bone metastases are treated new lesions can be formed by the settlement of CTC's in the bone or other tissues.

Radium-223 used against bone metastases today is a pure bone-seeker and do not address the problem of CTC's. Therefore there is a need in the field of alpha pharmaceutical bone therapeutics of a product that can also address CTC's.

The generation of daughter nuclides both in the injectates and in vivo is a potential problem for $^{224}$Ra and to a lesser extent $^{223}$Ra as the first progeny in the two decay series for both is radon which is highly diffusive. However literature data indicate that this is less of a problem when generated in vivo since radium is a bone volume-seeker and is embedded in the bone matrix. It also helps out that the uptake in skeleton of intravenous radium occurs almost instantly and intestinal, and to a less degree urinary, elimination happens rapidly, leading to an elimination from the blood within minutes after injection. It should be mentioned that urinary elimination is probably more pronounced in rodents compared to humans were fecal elimination is the main route. As reported by Nilsson et al (2005), a reduction of 88% of radium in blood at 10 minutes after injection occurs. When considering radium localized in the skeleton, it was for $^{223}$Ra reported equilibrium of $^{211}$Bi and $^{223}$Ra in bone after a few hours. For $^{224}$Ra based on animal data and extrapolation to adult human, it was found by two different models a $^{212}$Pb to $^{224}$Ra fraction of 0.88 and 1.0, i.e., almost complete retention of daughters. These data indicates a high retention of the daughter nuclides in bone for both $^{223}$Ra and $^{224}$Ra. For $^{224}$Ra a significant contribution to soft tissue uptake of progeny would therefore likely be from co-injected daughter nuclide. Thus it is imperative to develop methods to control daughter nuclides, at least $^{212}$Pb, in $^{224}$Ra injectates.

This has been achieved by the new $^{224}$Ra solutions described herein.

SUMMARY OF THE INVENTION

An object of the present invention is to provide a radiopharmaceutical solution comprising $^{224}$Ra and a complex capable of scavenging at least $^{212}$Pb.

In one embodiment of the present invention, the complex comprises one or more compounds selected from the group consisting of acyclic chelators, cyclic chelators, cryptands, crown ethers, porphyrins or cyclic or noncyclic polyphosphonates. DOTMP, EDTMP, bisphosphonate, pamidronate conjugated to DOTA or TCMC.

In another embodiment of the present invention, $^{212}$Pb and/or $^{212}$Bi is complexed by bone-seeking EDTMP.

In another embodiment of the present invention, the complexing agent is conjugated to a compound selected from the group consisting of a monoclonal, a polyclonal antibody, an antibody fragment, a synthetic protein, peptide, vitamin or vitamin derivative.

In another embodiment of the present invention, the complexing agent is the chelator TCMC conjugated to a compound selected from the group consisting of a monoclonal, a polyclonal antibody, am antibody fragment, a synthetic protein, peptide, vitamin or vitamin derivative.

One aspect of the present invention relates to a kit comprising a first vial comprising a radiopharmaceutical solution of the present invention, and a second vial comprising a neutralizing solution to adjust pH and/or isotonicity of the radiopharmaceutical solution prior to administration to a patient.

Another aspect of the present invention relates to a kit comprising a first $^{224}$Ra vial comprising a chelate labeled protein or peptide, a second vial comprising a solution.

A further aspect of the present invention relates to a radiopharmaceutical solution of the present invention for use as a medicament.

Yet another aspect of the present invention relates to a radiopharmaceutical solution of the present invention for use in treating skeletal disease.

In one embodiment of the present invention, the skeletal disease is selected from the group consisting of skeletal metastases from cancers to the breast, prostate, kidneys, lung, bone, or multiple myeloma, or non-cancerous diseases causing undesired calcification including ankylosing spondylitis.

A further aspect of the present invention relates to a method of treatment of malignant or non-malignant disease by administration of a radiopharmaceutical solution of the present invention to an individual in need thereof.

Another aspect of the present invention relates to a method for providing a $^{224}$Ra solution comprising protein-complex or peptide-complex comprising mixing of chelate labeled protein, e.g., a monoclonal antibody, or peptide with a solution comprising $^{224}$Ra.

BRIEF DESCRIPTION OF THE DRAWINGS

FIG. 3 A shows the biodistribution in nude mice of $^{224}$Ra and progeny $^{212}$Pb in a solution without chelator. FIG. 3 B shows biodistribution in nude mice of $^{224}$Ra solution containing EDTMP as chelator for progeny $^{212}$Pb. FIG. 3 C shows biodistribution in nude mice of $^{224}$Ra solution containing TCMC-trastuzumab (Herceptin) as chelator for progeny $^{212}$Pb.

FIG. 4 shows Table 1. Main radiation properties from the $^{224}$Ra series. $^1$Average per $^{224}$Ra transformation due to branching. Only X-rays or gammas above 1% effective abundance are accounted for. It adds up to a total effective energy of approximately 26.5 MeV of alpha of 0.7 MeV of beta per complete decay of $^{224}$Ra and daughters.

FIG. 5 shows Table 2. Ingrowth of $^{212}$Pb from a pure 10 MBq $^{224}$Ra source. Changes in activity level. Start activity 10 MBq pure 224-Ra.

FIG. 6A shows: Table 3 A. Thin layer chromatographic (TLC) profiles of $^{212}$Pb in a solution of $^{224}$Ra in equilibrium with progeny nuclides without and with complexing agents. Part 1: Phosphonates and formulation buffer (FB).

FIG. 6B shows: Table 3 B: Thin layer chromatographic (TLC) profiles of $^{212}$Pb in a solution of $^{224}$Ra in equilibrium with progeny nuclides without and with complexing agents. Part 2: Table 3 B shows TLC profiles for $^{212}$Pb in the presence of antibody-TCMC or DOTA conjugates and antibody without chelator.

FIG. 7 shows Table 4. Uptake ratios* for $^{212}$Pb for bone vs. blood and bone vs. kidneys.

Figure 1:
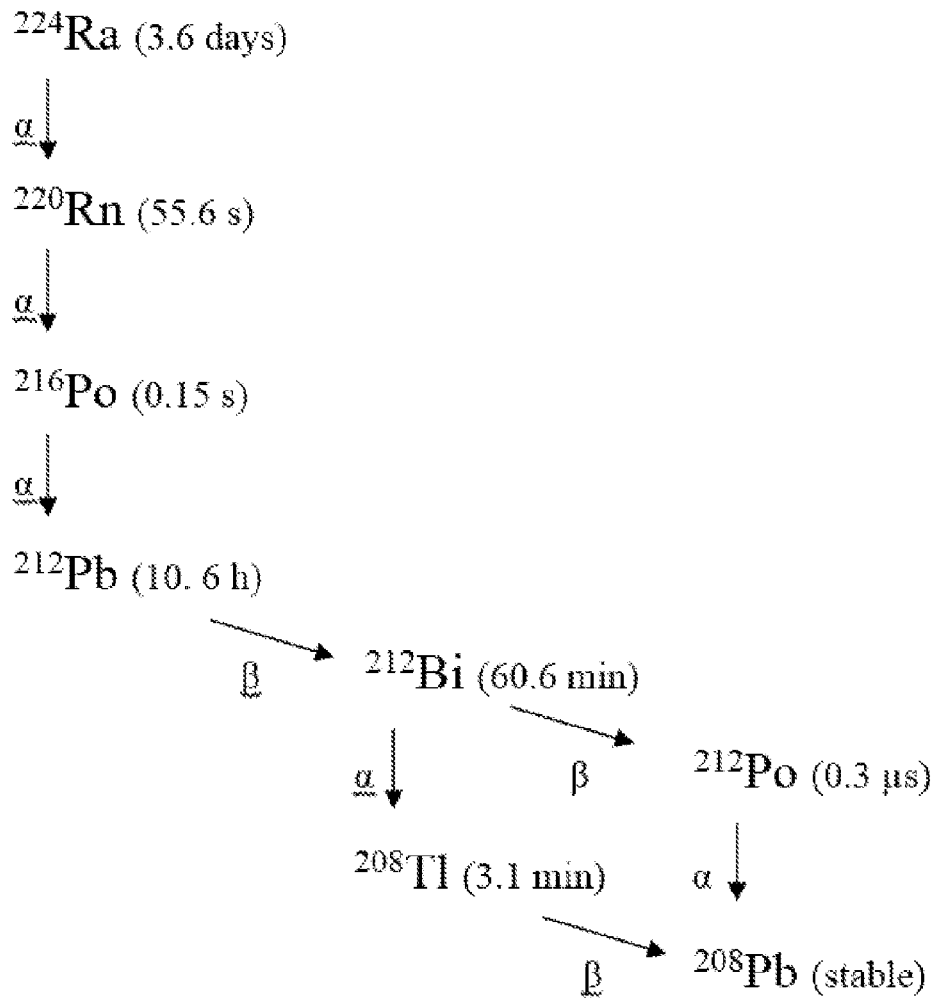
FIG. 1 shows the decay of $^{224}$Ra and daughters.
Figure 2:
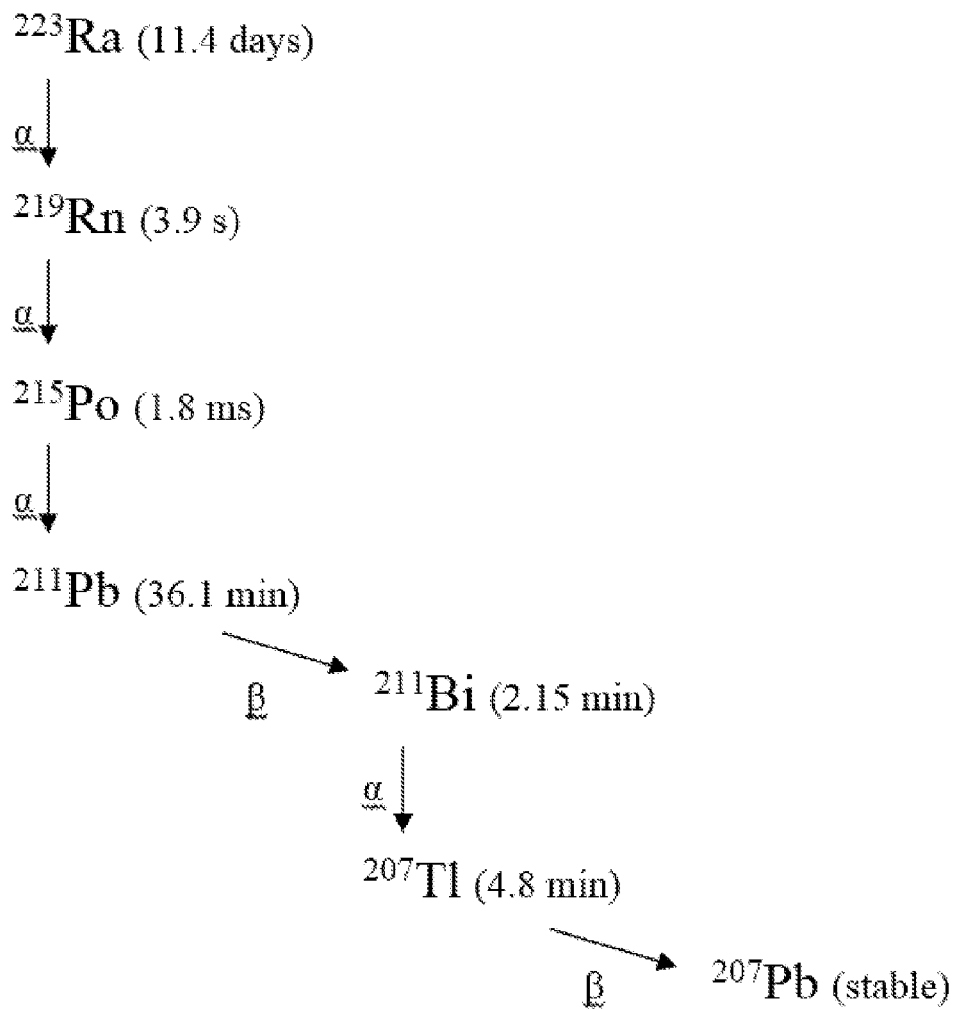
FIG. 2 shows the decay of $^{223}$Ra and daughters.

The present invention will now be described in more detail in the following.

DETAILED DESCRIPTION OF THE PREFERRED EMBODIMENT

Some Abbreviations Used

DOTMP—1,4,7,10-tetraazacyclododecane-1,4,7,10-tetra (methylene phosphonic acid)

EDTMP—ethylenediamine tetra(methylene phosphonic acid) EDTA —ethylenediaminetetraacetic acid p-SCN-Bn-DOTA—2-(4-isothiocyanatobenzyl)-1,4,7, 10-tetraazacyclododecane-1,4,7,10-tetraacetic acid DOTA-1,4,7,10-tetraazacyclododecane-1,4,7,10-tetraacetic acid and also used for benzyl-1,4,7,10-tetraazacyclododecane-1,4,7,10-tetraacetic acid conjugated to monoclonal antibody p-SCN-Bn-TCMC—2-(4-isothiocyanotobenzyl)-1, 4, 7, 10-tetraaza-1, 4, 7, 10-tetra-(2-carbamonyl methyl)-cyclododecane TCMC—1, 4, 7, 10-tetraaza-1, 4, 7, 10-tetra-(2-carbamonyl methyl)-cyclododecane and also used for benzyl-1, 4, 7, 10-tetraaza-1, 4, 7, 10-tetra-(2-carbamonyl methyl)-cyclododecane conjugated to monoclonal antibody mAb—monoclonal antibody The same abbreviations are in the following used for acids, salts or partly or fully dissociated versions of the chelators.

It has been an unexpected finding that it is possible to strongly complex daughter nuclide in the presence of radium with complexing compounds tested, EDTMP and monoclonal antibody conjugated to the TCMC and DOTA chelators, and at the same time keeping radium mainly as an uncomplexed cation fully targetable to bone.

A Radiopharmaceutical Solution

An object of the present invention is to provide a radiopharmaceutical solution comprising $^{224}$Ra and a complex capable of scavenging at least $^{212}$Pb.

In the present context is "scavenging" defined as at least 50% bound according to thin layer chromatography (TLC), centrifuge concentration separation or biodistribution profiles.

This means, as an example, at least 50% less blood uptake of $^{212}$Pb with a small molecular chelator. With an antibody conjugated chelator, where blood uptake is not a reliable indicator, at least 50% bound according to TLC analyses.

In one embodiment of the present invention is at least 60% bound.

In another embodiment of the present invention is at least 70% bound.

In another embodiment of the present invention is at least 80% bound.

In another embodiment of the present invention is at least 85% bound.

In another embodiment of the present invention is at least 90% bound.

The compound or compounds may also be capable of scavenging more radionuclides than $^{212}$Pb.

In one embodiment of the present invention, the complex comprises one or more compounds selected from the group consisting of acyclic chelators, cyclic chelators, cryptands, crown ethers, porphyrins or cyclic or noncyclic polyphosphonates. DOTMP, EDTMP, bisphosphonate, pamidronate conjugated to DOTA or TCMC.

In one embodiment of the present invention, the complex is at a concentration of 1 ng/mL to 1 g/mL.

In another embodiment of the present invention, the complex is at a concentration of 100 ng to 10 mg/mL The complex can comprise one, two, three, four, five or more compounds.

In another embodiment of the present invention, $^{212}$Pb and/or $^{212}$Bi is complexed by bone-seeking EDTMP.

In one embodiment is the solution in a volume of 100 µL to 1000 mL, such as 500 µL to 100 mL, 1 mL to 10 mL.

In one embodiment of the present invention is the radioactivity of the solution 1 kBq to 1 GBq, such as 10 kBq to 100 MBq, such as 100 kBq to 10 MBq.

In another embodiment of the present invention is the radioactivity of the solution 100 kBq to 100 MBq.

In another embodiment of the present invention, the complexing agent is conjugated to a compound selected from the group consisting of a monoclonal, a polyclonal antibody, an antibody fragment, a synthetic protein, a peptide, a hormone or hormone derivative or a vitamin or vitamin derivative, e.g., biotin and folate.

In another embodiment of the present invention, the complexing agent is the chelator TCMC conjugated to a compound selected from the group consisting of a monoclonal, a polyclonal antibody, am antibody fragment, a synthetic protein, a peptide, a hormone or hormone derivative or a vitamin or a vitamin derivative.

For dosing purposes $^{224}$Ra solutions administered should have been stored for some time, e.g., 1 day or more preferably at least two days, such as 1-2 days or 1-3 days, to reach equilibrium between $^{224}$Ra and $^{212}$Pb/$^{212}$Bi. This will ensure $^{212}$Pb to $^{224}$Ra activity ratios between 0.83 and 1.14. This can, e.g., be accomplished by the manufacturer by simply retaining the product for a day or so before shipment.

It is important to keep radium as mainly an uncomplexed, or weakly complexed cation as this ensures a maximum uptake in bone and bone metastases and also ensures favorable excretion of eliminated product mainly through the intestines.

By adding complexing agent to a solution of radium the radioactive daughter can be made bone- or tumor-seeking and increase the therapeutic potential of the radium solution instead of being a health hazard. It should be a complexing agent that does not negatively affect the bone-seeking properties of radium, though. For example can EDTMP scavenge $^{212}$Pb produced in the radium solution during transport and storage between the production site and the hospitals whereby the product is going to be administered.

Although it is possible to reduce the susceptibility by adding radiolytic inhibitors, tumor targeting proteins or peptides are often more susceptible to radiolysis and should probably be supplied in a kit format whereby they are added a few hours to a few minutes before administration of $^{224}$Ra solutions with relatively long shelf-lives.

It is known in the field that calixarenes and EDTA to some extent can complex radium and also complex lead and bismuth. However, in the current work we found chelators that would leave radium mainly uncomplexed or weakly complexed, as determined by in vivo biodistribution measurements, while being able to rapidly and with relevant stability, complex the longest living daughter $^{212}$Pb. The selective complexation can be used to make at least lead bone- or tumor-seeking while maintaining the favorable properties of radium in terms of treating sclerotic diseases, like skeletal metastases. The $^{212}$Pb complex that targets bone or tumor cells generates the alpha emitter $^{212}$Bi from the decay of $^{212}$Pb. Thus, the beta emitter $^{212}$Pb is used as an indirect alpha source for irradiating the targeted cells or tissue. Other potential chelates which could be suitable for $^{224}$Ra daughter nuclide scavenging besides TCMC and DOTA includes but are not limited to phorphyrins, DTPA and DTPA derivatives and also carboxyl linked DOTA.

Lead-212 is by far the longest living of the progenies from $^{224}$Ra and this is the most important to complex, as it is an in vivo generator for the short lived alpha-emitter $^{212}$Pb-chelate is taken up in bone or in tumor cells $^{212}$Bi will also likely be retained in the target. In a $^{224}$Ra solution in equilibrium with progenies there will be more than 10 times of $^{212}$Pb vs. $^{212}$Bi atoms. Thus, the amount of radiation generated from the $^{212}$Bi atoms in these solutions are modest and probably not of a toxicologically importance compared with $^{224}$Ra and $^{212}$Bi decay series. The amount of $^{212}$Bi is comparable to that of the $^{211}$Pb which indirectly produces an alpha particle in the $^{223}$Ra series and this has not been of a significant problem for the registration and clinical use of $^{223}$Ra in equilibrium with progenies.

If, however, a high degree of chelation also of $^{212}$Bi in an injectate should be needed, it may at least in some instances be necessary to add a stabilizing agent like NaI or HI since bismuth in aqueous solutions tends to exist in a state less suitable for chelation.

When comparing with current approved alpha-pharmaceutical for treatment of skeletal metastases, i.e., $^{223}$Ra, the novel solutions described herein could give, in one of the embodiment, a product with improved properties for treatment of skeletal metastases since the daughter nuclide can be made targetable to circulating cancer cells and, to some extent, also soft tissue metastases. This may prevent recurrence from cancer recolonization of the skeleton due to CTC's.

Another aspect is that the shorter half life of $^{224}$Ra vs. $^{223}$Ra may actually be of some benefit as the radium is embedded in the bone matrix. Because of the high density of the bone mineral the range of alpha-particles is strongly reduced in bone vs. soft tissues. Especially in rapid mineralizing areas like osseous cancer metastases, the embodiment process may be of significance when using a volume-seeking alpha-pharmaceutical.

Therefore, $^{224}$Ra could improve the tumor dose since, on average, it will be less embedded at the time of decay.

Diseases by which the novel $^{224}$Ra solutions may be used include but are not limited to primary and metastatic cancers, autoimmune diseases and artherioschlerosis. The product may be administered intravenously or locally, including intraperitoneally, or in limb perfusion settings.

The chelators used in the novel solutions may be acyclic as well as cyclic chelators and cryptands, crown ethers, porphyrins or cyclic- or noncyclic polyphosphonates including DOTMP and EDTMP. Also a bisphosphonate, e.g., pamidronate, conjugated to DOTA, TCMC or similar may be used as scavenger in the $^{224}$Ra solution.

One may argue that the amount of $^{212}$Pb in therapeutic $^{224}$Ra solution may be moderate to modest (i.e., at equilibrium about 1.1 times that of $^{224}$Ra). If one assume similar dosing of $^{224}$Ra as is done with $^{223}$Ra in patients but correct for the half life difference, roughly 150 kBq per kg of bodyweight would be the administered dose.

At equilibrium this would translate into a $^{212}$Pb-antibody conjugate dosage of 11.5 MBq in 5 liters of blood in a 70 kg patient (if $^{212}$Pb is quantitatively chelated). The number of circulating tumor cells is typically less that 10 cells per ml thus in 5 l blood there are less than 50 000 tumor cell in total. If only 1 in 100 000 of the injected $^{212}$Pb-antibody conjugate molecules binds to the tumors cells this would mean at least 0.0023 Bq per cell, equivalent to approximately 127 $^{212}$Pb atoms bound per cell, which would be highly destructive as it has been reported that a mean of 25 cell bound $^{212}$Pb per cell would kill 90% of a cell population.

Previously it was suggested to combine radium and phosphonates and more preferentially bisphosphonates in the treatment of skeletal metastases of cancer. However, it was suggested to use the two compounds separated from each other as it was preferred to inject at different time points. The application of phosphonates was not indicated for radionuclide complexation. The main purpose was to use pharmacologically active amounts of phosphonates as a secondary bone treatment to radium. Also it was preferred to use a non-complexing bisphosphonates, thus this teaches away from using EDTMP or similar as additive to radium solutions for the complexation of daughter nuclides. At the time it was common knowledge that EDTMP could complex alkaline earth metals, as it was known in the field that $^{153}$Sm-EDTMP can cause complexing of calcium in blood and cause hypocalcemia.

However, in the current work we have shown that when modest amounts of EDTMP is used, it is possible to complex $^{212}$Bi and $^{212}$Pb without significantly reducing the bone-seeking properties of $^{224}$Ra.

The current report is the first time the addition of a complexing phosphonate to a radium solution has been presented. It shows that it is possible to obtain selective complexation of daughter nuclide without significantly alter the bone targeting properties of radium. This is important since although complexing phosphonates are bone-seekers, radium shows an even higher bone targeting ability than the phosphonates. It is therefore highly advantageous that the labeling of daughter nuclides does not cause reduced skeletal uptake of the radium.

As for bone targeting with phosphonates it is known in the field that radionuclides like $^{177}$Lu, $^{153}$Sm, $^{227}$Th, and $^{225}$AC complexed with phosphonates can target bone. In a previous report it was also shown that the radionuclides $^{212}$Pb and $^{212}$Bi could be complexed with EDTMP and DOTMP. However the labeling was performed with high pH and also needed to be purified by ion exchanger after labeling. Thus this teaches away from using in situ labeling in the presence of radium, without affecting radium, and without purification as is shown in the current application. Thus, we hereby present a novel way of using EDTMP as a scavenger for daughter nuclides in $^{224}$Ra solutions which (1) improve the bone dose per unit $^{224}$Ra administered, and (2) strongly reduce uptake of $^{212}$Pb in hematopoietic cells and tissues in effect causing better target to non-target radiation ratios.

The solutions used for $^{224}$Ra and the daughter nuclide complexation may contain radiolytic inhibitors and other modificators suitable for a medical injectate known in the field.

The solution can also be a pharmaceutical composition.

Usually is an important element of a pharmaceutical composition a buffer solution, which to a substantial degree maintain the chemical integrity of the radioimmunoconjugate and is being physiologically acceptable for infusion into patients.

In one embodiment of the present invention the pharmaceutical composition comprises one or more pharmaceutically acceptable carriers and/or adjuvants.

Acceptable pharmaceutical carriers include but are not limited to non-toxic buffers, fillers, isotonic solutions, etc. More specifically, the pharmaceutical carrier can be but are not limited to normal saline (0.9%), half-normal saline, Ringer's lactate, 5% Dextrose, 3.3% Dextrose/0.3% Saline. The physiologically acceptable carrier can contain an anti-radiolytic stabilizer, e.g., ascorbic acid, which protect the integrity of the radiopharmaceutical during storage and shipment.

Kits

The solution should be made physiologically suitable for injections either at a centralized production site or be made up by a kit system of typically 2-4 vials whereby being physiologically suitable for injection after combination of the kit vials.

One aspect of the present invention relates to a kit comprising a first vial comprising a radiopharmaceutical solution of the present invention, and a second vial comprising a neutralizing solution to adjust pH and/or isotonicity of the radiopharmaceutical solution prior to administration to a patient.

Another aspect of the present invention relates to a kit comprising a first vial comprising a chelate conjugated to a protein or peptide or mixtures of proteins or peptides, and a second vial comprising a $^{224}$Ra solution.

Since the decay series of $^{224}$Ra includes a radon daughter which may diffuse into the air, vials containing the products must be well sealed to prevent escape of $^{220}$Rn.

Because of the highly localized nature of alpha-irradiation, radiolysis must be considered as a potential problem and the radiopharmaceutical must be designed to minimize this. According to the knowledge in the field radiolabeled antibodies are sensitive to radiolysis and therefore a kit system may be advantageous for $^{224}$Ra solutions which are to be combined with chelator conjugated antibodies for scavenging $^{212}$Pb and or $^{212}$Bi.

For a monoclonal antibody it is usually advisable be keep the self dose of the alpha particle producing radiopharmaceutical solution below 0.5 kGy to avoid reduced binding properties due to radiolysis. Thus, a kit system whereby chelator conjugated antibody is added to the $^{224}$Ra (including daughters) solution a few hours to 10 minutes before injection is advised for concentrated solutions intended for remote shipping.

In one embodiment of the present invention, the chelator conjugated antibody is added to the $^{224}$Ra (including daughters) solution 30 min to 1 hour before injection.

In one embodiment of the present invention, the chelator conjugated antibody is added to the $^{224}$Ra (including daughters) solution 1 min to 20 min before injection.

In one embodiment of the present invention, the chelator conjugated antibody is added to the $^{224}$Ra (including daughters) solution 1 min to 10 min before injection.

A kit with a chelate labeled protein or peptide in one vial and a $^{224}$Ra solution in another vial whereby the content of the two are mixed a few hours to 30 minutes before administration to a patient as to bind $^{212}$Pb and or $^{212}$Bi to the chelate.

In one embodiment of the present invention, the content of the two are mixed 30 min to 1 hour before injection.

In one embodiment of the present invention, the content of the two are mixed 1 min to 20 min before injection.

In embodiment of the present invention, the content of the two are mixed 1 min to 10 min before injection.

Optionally, a third vial containing a liquid used for dilution and isotonicity adjustment before administration of the radiopharmaceutical solution could be used. This third vial may contain EDTMP which could chelate $^{212}$Bi, if needed.

Medical Uses

The described novel methods and solutions have thereby solved a major problem for the application of $^{224}$Ra in nuclear medicine.

Thus two types of diseases can be treated with the new formulations:
1. Pure bone related, or sclerotic diseases with radium and daughter nuclide complexed by a phosphonate.
2. Bone-related disease with soft tissue or circulating target cells components by radium and daughter nuclide complexed to chelate-monoclonal antibody conjugate or similar protein or peptide conjugates. A special embodiment of this would be when $^{212}$Pb is conjugated to a protein or peptide chelate and the $^{212}$Bi is complexed by a bone seeker, e.g., EDTMP.

Proteins or peptides may be used with the current invention including those targeting osteosarcoma, lung cancer, breast cancer, prostate cancer, kidney cancer, thyroid cancer.

Thus, a further aspect of the present invention relates to a radiopharmaceutical solution of the present invention for use as a medicament.

Yet another aspect of the present invention relates to a radiopharmaceutical solution of the present invention for use in treating skeletal disease.

In one embodiment of the present invention, the skeletal disease is selected from the group consisting of skeletal metastases from cancers to the breast, prostate, kidneys, lung, bone, or multiple myeloma, or non-cancerous diseases causing undesired calcification including ankylosing spondylitis.

A further aspect of the present invention relates to a method of treatment of malignant or non-malignant disease by administration of a radiopharmaceutical solution of the present invention to an individual in need thereof.

Method of Production

Herein are described novel methods possible to produce a $^{224}$Ra solution suitable for treating skeletal diseases including primary or metastatic cancer, using centralized production and up to several days of shipment and or storage before administration to patients.

Moreover, such a solution can give higher initial tumor radiation dose compared to a pure $^{224}$Ra solution since the daughter products will give additional dose to tumor when they are made bone-seeking or tumor seeking by the aforementioned chelating complexes. This could make $^{224}$Ra solutions more potent in cancer therapy since the mother nuclide can target the bone disease while the longest lived daughter nuclide can by an added complex be made to seek out and destroy circulating cancer cells in the blood, alternatively be made a purer bone-seeker by phosphonate complexation.

The novel procedures and methods presented here allows the production and shipment of $^{224}$Ra with longer shelf life of days or even up to a week or longer since the "problematic" daughter nuclide can be scavenged by tumor-seeking chelates and actually enhance the therapeutic properties of the $^{224}$Ra solutions.

This finding is important since $^{224}$Ra has been considered less useful for e.g., cancer therapy against skeletal metastases because of daughter products with substantial half-lives, in particular $^{212}$Pb, which will be present in significant quantities a few hours after the production of a pure $^{224}$Ra solution.

That is made possible by the novel pharmaceutical solutions described here were the $^{224}$Ra targets bone and bone metastases while $^{212}$Pb can be made to target circulating tumor cells depending on the chelate-antibody conjugate used. The pharmaceutical solution could be "taylor made" according to the primary tumor from which the skeletal metastases originate. There exist several antibodies with selectivity for different antigens expressed in e.g., prostate-, breast-, lung-, bone-, kidney-, thyroid- and multiple myeloma cancers.

Thus, another aspect of the present invention relates to a method for providing a $^{224}$Ra solution comprising protein-complex or peptide-complex comprising mixing of chelate labeled protein or peptide with a solution comprising $^{224}$Ra.

Thus, the novel invention described herein can be used either as a pure bone-seeker when combined with EDTMP or similar, or if patients have measurable CTC's or is suspected of such, can be used as a combination of treatment of bone metastases and CTC's or soft tissue metastases, thereby adding a new dimension to alpha pharmaceuticals against bone related disease, i.e., an additional prophylactic activity preventing settling of viable CTC's in the skeleton or soft tissues.

The novel and surprising findings are as follows:
1. Radium solutions can be conditioned with complexing phosphonates or complex conjugated antibodies without causing complexation of radium and causing reduced bone uptake of radium while complexing $^{212}$Pb and/or $^{212}$Bi in situ without a need for purification before use.
2. Daughter nuclides produced during shipment and storage can be complexed effectively in situ yielding a radium solution with improved daughter nuclide properties.

The $^{224}$Ra solution can be stored or shipped for several days and still the major fraction of the $^{212}$Pb generated can be complexed, i.e., at least 60%, more favorable at least 90%, and even more favorable 95-100%, depending on the amount of complexing agent added.

This is important since it gives a radiopharmaceutical with better overall target to non-target ratios compared to existing radium formulations as shown in following examples and allows the use of $^{224}$Ra solutions that has been shipped and stored for several days. Indeed it teaches away from using freshly prepared $^{224}$Ra solutions with only few hours shelf life as in the method of Altmann Terapie, since it may be advantageous with the new method that $^{212}$Pb has reached equilibrium or close to equilibrium, i.e., at least 1 day or more, to obtain a reproducible and defined ratio between $^{224}$Ra and $^{212}$Pb in the administered radiopharmaceutical solution.

We have also confirmed that other complexes than phosphonates can be labeled with daughter nuclide in situ in radium solutions without significantly affecting the radium, e.g., chelate-antibody conjugates were added to radium solution and showed a relevant labeling of daughter nuclide with a significant preservation of the chemical integrity of radium, thus it is possible to have a radium solution whereby one or more of the daughter nuclides is complexed to tumor-seeking molecules yielding a pharmaceutical solution with bi-specific targeting properties, e.g., radium targeting the skeletal disease and a chelate complex with daughter nuclides targeting a tumor cell antigen on circulating tumor cells etc. As a special embodiment one daughter nuclide can be complexed to a monoclonal antibody and the other to a phosphonate.

In a special embodiment of the current invention is a solution with radium containing TCMC conjugated to a protein or a peptide, preferentially a monoclonal antibody, whereby the antibody is targeting an antigen on breast-, prostate-, lung-, kidney-, bone- or multiple myeloma cancer cells. If left for a few minutes to a few days, the $^{212}$Pb generated will mainly bind to the TCMC-antibody conjugate. When such a solution is injected into a cancer patient, $^{224}$Ra will protect the bone from destruction by killing tumor cells at the bone surface and in the skeleton and the $^{212}$Pb labeled antibody will kill circulating cells out of range from the radium radiation. Thus, what was before a problem of free daughter nuclides with undesired biodistribution is made into an advantage for the $^{224}$Ra series by the use of the current invention. It is particularly attractive to use an internalizing antigen as target since $^{212}$Pb-conjugates are especially effective as in vivo generator for alpha-emitters under such conditions whereby the alpha emitting $^{212}$Bi daughter is enclosed in the target cells (Boudousq et al., 2013).

In one embodiment the radiopharmaceutical product is shipped ready to use, e.g., in a vial with a septum for withdrawal of the solution with a syringe or even as a prefilled syringe ready to use. In a second embodiment the product may be shipped in a kit format consisting of a vial with $^{224}$Ra solution, a second vial with a solution of a chelator and optionally a third solution with a formulation buffer for the adjustment of concentration and/or pH etc. The chelator, whereby it is a phosphonate, chelator-antibody conjugate or similar, is added to the Ra solution and mixed for a few minutes to a few hours most preferable from 5 –60 minutes, before the product is, if needed added a formulation buffer, and administered to the patient.

EXAMPLES

Example 1

Calculation of the $^{212}$Pb Daughter Nuclide Level from $^{224}$Ra Decay at Various Time Points Background. The $^{212}$Pb produced after preparation of a pure $^{224}$Ra radiopharmaceutical may be a problem since it has different and undesirable properties compared with the mother nuclide. E.g., it is known that radium can target bone and bone metastases, but the lead progeny has undesired accumulation in hematopoietic cells and tissues and in the kidneys.

Method: The ingrowth of $^{212}$Pb from a pure $^{224}$Ra source were calculated using a universal activity calculator.

Results: Table 2 shows the amount of $^{212}$Pb at various time points after the production of a pure $^{224}$Ra pharmaceutical solution and storage in a gas tight container.

The data shows that significant amount of daughter nuclide is present within a relatively short time frame, complicating a potential centralized production and supply of $^{224}$Ra based radiopharmaceuticals. It is noteworthy though that the ratio of $^{212}$Pb to $^{224}$Ra in the solution reaches 1 after 36 hours and thereafter gradually increases to about 1.1 of which it stay for the rest of the time until complete decay.

Example 2

Preparation of Radionuclides and Counting of Radioactive Samples

In the following, all work with the concentrated radioactive preparations including evaporation of solvent etc was performed in a glove-box. A source of $^{228}$Th in 1 M HNO$_3$ was acquired from a commercial supplier. Ac-resin was obtained from Eichrom Technologies LLC (Lisle, Ill., USA) in the form of a pre-packed cartridge.

To use smaller volume of solvent, about thirty percent of the materials in a cartridge (Cartridge 1) was extracted and repacked in a smaller column (Cartridge 2) made by a 1 ml filtration column (Isolute SPE, Biotage AB, Uppsala, Sweden). A slurry representing 20% of the original cartridge content was used for immobilizing of $^{228}$Th in 500 mikroliter 1 M HNO$_3$ which was added 500 microliter of 1 M HCl and incubated by shaking the vial (4 ml vial, E-C sample, Wheaton, Millville, N.J., USA) for at least 4 hours. Cartridge 2 was added a small amount (about 0.1 ml) of the Ac-resin. Thereafter, the slurry was added to cartridge 2 using the prefilled material as a catcher layer. Radium could be eluted from the Cartridge 2 in 2 ml of 1 M HCl. The 2 ml radium solution was evaporated to dryness, using a heater block and flushing the vial with N2 gas through a Teflon tube inlet and outlet in the rubber/Teflon septum on the vial and by leading the acid vapor into a beaker of saturated NaOH by a stream of N$_2$-gas.

The residue was resolved in 0.5 ml 1 M HNO$_3$ and loaded to a cartridge 3 consisting of a 1 ml Isolute column packed with about 250 mg Dowex anion exchanger. Cartridge 3 was washed with 7 ml 1 M HNO$_3$, which removed $^{212}$Pb, and finally with 3-4 ml 8 M HNO$_3$ to elute $^{224}$Ra. The $^{224}$Ra eluate was evaporated to dryness, using the heater block and a flow of N$_2$-gas, and the residue could be dissolved in 0.1 M HCl. Typically, more than 70% of the $^{224}$Ra present in the $^{228}$Th source could be extracted and purified using the described methods.

Radioactive samples were counted on a Cobra II Autogamma counter (Packard Instruments, Downer Grove, Ill., USA). During extraction of $^{224}$Ra from the $^{228}$Th source, a CRC-25R dose calibrator (Capintec Inc., Ramsey, N.J., USA) was used.

To determine distribution of $^{224}$Ra, $^{212}$Pb and $^{212}$Bi in real time in samples, a liquid nitrogen cooled HPGe detector (GWC6021, Canberra Industries, Meriden Conn., USA) was used. This was combined with a DSA 1000 digital signal analyzer and the Genie 2000 software (Canberra).

Example 3

Determining Net Count Rate for $^{212}$Pb in a $^{212}$Pb/$^{224}$Ra Mixture Before Radioactive Equilibrium has been Reached After more than 3 days, i.e., "equilibrium" a sample will for practical purposes have 1.1 times $^{212}$Pb vs $^{224}$Ra.

Regardless of whether $^{212}$Pb is higher or lower than equilibrium it can be assumed that this is reached after 3 days since surplus $^{212}$Pb is reduced by 99% and the ingrowth of $^{212}$Pb from $^{224}$Ra is practically complete vs. "equilibrium".

Using the Cobra II Autogamma counter with a counting window setting from 70-80 KeV gives mainly the $^{212}$Pb with very little contribution from other radionuclides in the $^{224}$Ra series. Radium-224 must be indirectly counted when the initial $^{212}$Pb has vanished and equilibrium between $^{224}$Ra and $^{212}$Pb has been reached (after approximately 3 days). This indirect counting requires the sample to be stored in a relatively gas tight containers as otherwise the $^{220}$Rn may escape preventing the radionuclide equilibrium of 1.1 between $^{212}$Pb and $^{224}$Ra to be reached.

Since sampling and counting may be separated by some time, the net count rate for $^{212}$Pb can be adjusted for decay to determine the net $^{212}$Pb count rate at the time of sampling.

Example 4

Thin Layer Chromatography Analyses

Thin layer chromatography (TLC) was performed using chromatography strips (model #150-772, Biodex Medical Systems Inc, Shirley, N.Y., USA). A small beaker with about 0.5 ml of 0.9% NaCl was used to place strips with a sample spot in. To the strip was typically added 1-4 μl of sample at approximately 10% above the bottom of the strip. After the solvent front had moved to about 20% from the top of the strip, the strip was cut in half and each half was placed in a 5 ml test tube for counting. In this system radiolabeled antibody and free radionuclide does not migrate from the bottom half while radionuclide complexed with EDTA migrates to the upper half. A formulation buffer (FB) consisting of 7.5% human serum albumin and 5 mM EDTA in DPBS and adjusted to approximately pH 7 with NaOH was mixed with the antibody conjugates in ratio 2:1 for at least 5 minutes before application to the strips to determine free radionuclide.

The analysis of the EDTMP was done without the FB (Table 3 A). The labeling of radionuclide with EDTMP was measured by the amount of migration to the upper half of strips. The DOTMP migrated poorly in this system and therefore these solutions had to be treated with FB to measure free radionuclide at the upper half of the strip (Table 3 A).

Example 5

In Situ Chelation of $^{212}$Pb in $^{224}$Ra Solutions

Initially $^{224}$Ra solutions in 0.1 M HCl was neutralized with 1 M NaOH and the EDTMP was added to the solution to obtain a pH slightly below neutral. In later experiments 10:1 ratio of $^{224}$Ra in 0.1 M HCl and 5 M ammonium acetate was used before addition of the chelators, resulting in a pH range of 5.5-7 for the reactions. Reaction times of 30 minutes to several days, at room temperature, were tested for EDTMP with good labeling yield (typically above 90% according to TLC) when concentrations of about 4-8 mg/ml EDTMP in reaction solutions were used. Thus, EDTMP seems to be a good scavenger for $^{212}$Pb in situ in $^{224}$Ra solutions. As for DOTMP the labeling was less efficient with about 70% labeling for 7 mg/ml at room temperature and about 1 h of reaction time. The labeling yield of DOTMP may be improved by adjusting chelator concentration or reaction time etc. It should be noted that subsequent experiments using EDTMP and ammonium acetate buffers showed a good labeling with $^{212}$Pb also in radium solutions of pH 5.5 to 7 as determined by thin layer chromatography (Table 3 A).

Long term scavenging was tested by leaving a $^{224}$Ra solution with EDTMP (approximately 6 mg/ml) buffered to about pH 6 with ammonium acetate, for 7 days at room temperature. Analysis of the $^{212}$Pb distribution profile was performed by use of TLC as described. Results: At least 93% of the activity was found in the upper half of the TLC-strip corresponding to EDTMP associated activity after 7 days. In conclusion, it is possible to effectively chelate $^{212}$Pb generated in situ in $^{224}$Ra solution by EDTMP. Thus, it is possible to prepare ready to use $^{224}$Ra solutions with a bone-seeking chelator that scavenge $^{212}$Pb in situ thereby obtaining $^{224}$Ra solution with improved shelf life for use as a bone targeting radiopharmaceutical.

As an alternative, a labeling kit may be used whereby EDTMP is added to a several days old $^{224}$Ra solutions a few minutes to a few hours before administration. Such a labeling kit will also allow centralized production of $^{224}$Ra as the kit can be very simple to use for $^{224}$Ra solutions several days to more than a week after the production date for $^{224}$Ra.

In an experiment with an 8 day old $^{224}$Ra solution in 0.1 M HCl and 0.5 M ammonium acetate, EDTMP to a concentration of about 7 mg/ml was added. After 10 minutes and 1 hours standing at room temperature, TLC analyses showed 91% and 93%, respectively, of the $^{212}$Pb was associated with the EDTMP.

EDTMP solutions up to 4 months old were tested and found to be functional, thus EDTMP seems well suited to be used in a kit format.

Example 6

Biodistribution in Mice of $^{224}$Ra with Significant Amounts of $^{212}$Pb with and without EDTMP The main objective was to study the biodistribution of the injected radionuclides with or without EDTMP. An EDTMP containing—and a saline control solution, respectively, of $^{224}$Ra in equilibrium with daughter radionuclides were used.

Materials and methods: Animal experiments were performed according to European regulations for animals used for scientific purposes. Nude mice were fully grown and were at an age of more than 6 months. A 3 day old 0.1 M solution containing $^{224}$Ra was split in two. One fraction was added EDMP and 1 M NaOH to adjust the pH to approximately 8, to a final concentration of 5 mg EDTMP per ml (solution A). The other fraction was adjusted by 1 M NaOH to approximately pH 7 (solution B). Each solution was sterile filtered through a 13 mm 0.2 µm Acrodisc syringe filter (Pall Life Science, Port Washington, N.Y., USA) with Supor membrane. Thereafter 100 µl with approximately 20 kBq of $^{224}$Ra were administered by tail vein injection into each mouse.

Results: As shown in FIGS. 3 A and B there was a significant improvement in $^{212}$Pb distribution when EDTMP was added. The soft tissue and blood uptake was significantly reduced while the bone targeting was similar as free $^{212}$Pb. Thus, the bone to soft tissue ratios were greatly improved for $^{212}$Pb, by adding EDTMP to the $^{224}$Ra solution. There is no significant change in the $^{224}$Ra distribution when adding EDTMP as shown in FIGS. 3 A and B.

Conclusion: addition of EDTMP to $^{224}$Ra solutions improves $^{212}$Pb biodistribution with no significant changes to the $^{224}$Ra biodistribution.

Example 7

Labeling of Chelator-Conjugated Antibody with $^{212}$Pb In Situ in $^{224}$Ra Solution Background: It is advantageous from a logistic perspective that radiopharmaceutical can be produced in a centralized production unit and shipped to the end user. The $^{212}$Pb generated should be scavenged by the chelator to minimize injection of free $^{212}$Pb when $^{224}$Ra is used.

Methods: $^{224}$Ra was produced and purified as described in example 2. TCMC- and DOTA-labeled monoclonal antibodies were prepared by using antibodies purified with centrifuge concentrator (Vivaspin 4 or 20, 50 000 MWCO, Sartorius Stedim, Goettingen, Germany) and added 150 mM carbonate buffer, pH 8.5-9. The antibody had a concentration of typically 20-30 mg/ml and was added p-SCN-Bn-TCMC or p-SCN-Bn-DOTA (Macrocyclics Inc, Dallas, Tx, USA) using antibody to chelator ratios of 1:9 or 1:5, respectively. After at least two hours incubation at room temperature the reaction was terminated by adding 0.1 M glycine in carbonate buffer (pH approximately 8.5) and further incubation for 10 minutes before purification and buffer exchange into 0.9% NaCl using centrifuge concentrator (Vivaspin). Chelator-antibody concentrations of 15-35 mg/ml in 0.9% NaCl were used as stock solutions.

To a 2 ml eppendorf tube was added typically 40 µl $^{224}$Ra in 0.1 M HCl, 5 µl of 5 M ammonium acetate, 5-10 µl, (15-30 mg/ml) TCMC- or DOTA-labeled antibody in 0.9% sodium chloride. This method was tested for 4 different antibody conjugates including those of trastuzumab (Herceptin), rituximab, cetuximab, and 01-3 murine monoclonal antibody. The pH was determined to be in the range of 5.4-6.0 by applying 1 µl on a pH paper (No 1.09564.0003 and 1.09556.003 from Merck KGaA, Darmstadt, Germany) and reading the colour. The reaction was performed at room temperature.

In some of the experiments a control solution with the same ingredients except for that the antibody did not contain TCMC or DOTA was reacted in parallel using the same conditions. After 30 and 100 minutes 5 µl was withdrawn and mixed with 10 µl of a formulation buffer (FB) consisting of 7.5% human serum albumin and 5 mM EDTA in DPBS. After at least 10 minutes, 1-4 µl of the product/FB mixture was withdrawn and placed on a thin layer chromatography strip (Biodex). The same procedure was performed with the control solution. The strips were eluted in 0.9% NaCl solution and when the solvent front reached almost to the top, the strip was removed, cut in half and the bottom and top part was counted separately on a Cobra II gamma counter (as previously described).

Results: The thin layer profiles are presented in Table 3 B. Typically more than 90% of the activity was found at the bottom half of the thin layer strip for the TCMC- and DOTA-antibody conjugate. In the control, typically more than 97% of the activity was found in the top half of the strip. This shows that both TCMC- and DOTA-conjugated antibodies can be efficient scavengers for $^{212}$Pb in $^{224}$Ra solution. Using a centrifuge filtering unit with a cut-off of 37 kDa it was also shown that $^{224}$Ra in the reaction solution could be separated effectively from the TCMC- or DOTA conjugates by washing with 0.9% NaCl solution. By using 2 ml and concentrate to 0.25 ml>85% of the radium was removed from the $^{212}$Pb-DOTA-antibody conjugate, thus it shows that TCMC- and DOTA-antibody conjugates can scavenge $^{212}$Pb without significantly complexing $^{224}$Ra. In conclusion, it is possible to use TCMC or DOTA-antibody conjugate to scavenge $^{212}$Pb in $^{224}$Ra solution thus, enabling the production of a pharmaceutical solution with dual targeting properties, i.e., a bone seeking $^{224}$Ra and an antigen seeking $^{212}$Pb conjugate.

In a follow-up experiment a $^{224}$Ra solution, added TCMC-labeled chOI-3 (chimeric OI-3) monoclonal antibody conjugate (to about 1.5 mg/ml), buffered to about pH 5.5 with ammonium acetate and kept for 7 days at room temperature. Thereafter samples were withdrawn and mixed 1:2 with formulation buffer (as described) and after 5 minutes or more applied on TLC strips as described. It was found that on average 95.6% was retained with the protein (lower half of the strip). In conclusion $^{212}$Pb is scavenged effectively in situ in $^{224}$Ra solution over several days by TCMC-labeled antibody. Thus, it shows that centralized production requiring storage and shipment for several days is possible for $^{224}$Ra solutions with chelate-antibody conjugate.

Example 8

Cell Binding Experiment with Radiolabeled Monoclonal Antibody in Mixture with $^{224}$Ra The human osteosarcoma cell line OHS expresses Her-2 (relatively weak) and MUC-18 (moderate). They were therefore used for evaluating cell binding fraction of chelator conjugated trastuzumab and chOI-3 antibodies against Her-2 and MUC-18, respectively. Radium-224 was dissolved in 0.1 M HCl and left for two days to reach equilibrium with $^{212}$Pb and $^{212}$Bi. To adjust pH 12 µl 5 M ammonium acetat in metal free water was added to 100 µl of $^{224}$Ra in 0.1 M HCl and thereafter added 200 µg of TCMC-labeled trastuzumab. After 30 minutes thin layer chromatography confirmed that more than 90% of the $^{212}$Pb was scavenged by the chelator. The reaction mixture was sterile filtered using a 13 mm syringe filter and the product tested for cell binding using approximately 10 million cells in 0.2 ml of DPBS with 0.5% BSA. Cells were either blocked by incubation with 20 µg of the same antibody for 15 minutes (to measure non specific binding) or left unblocked before adding reaction solution with about 10 ng of chelate-antibody conjugate mixed with radionuclide to each tube. After 1 hour of incubation, tubes were counted on the Cobra II gamma counter to determine added activity. Thereafter the cells were washed three times with 0.5 ml DPBS/0.5% BSA by whirlmixing, centrifugation and removal of supernatant and then the cell bound activity in the tubes were measured. The percent of cell bound antibody conjugate was determined as bound after wash divided by the added activity times 100. Results: When corrected for decay and radiochemical purity and the non-specific binding was subtracted, it was found that 64.3-72.2% of the $^{212}$Pb-labeled antibodies were bound specifically to the cells. In this one point assay this indicates appropriate targeting properties of the $^{212}$Pb-antibody conjugate produced in situ in $^{224}$Ra solutions. Conclusion: It is shown that $^{212}$Pb-labeled conjugates with relevant tumor targeting properties can be produced in situ in $^{224}$Ra solutions.

Example 9

Biodistribution in Mice of $^{224}$Ra/$^{212}$Pb with TCMC-Labeled Monoclonal Antibody Background: To study whether $^{224}$Ra/$^{212}$Pb solutions could be used for preparing skeletal targeted and tumor cell targeted co-therapeutics.

Materials and Methods: A one day old $^{224}$Ra solution as described in example 6 was added NaOH, 5 M ammonium acetate and TCMC-labeled Trastuzumab in the same way as in example 7 and stored over night. The solution was added metal free water in a 1:1 ratio, sterile filtered using a 13 mm 0.2 µm Acrodisc syringe filter (Pall Life Science, Port Washington, N.Y., USA) with Supor membrane. The cell binding ability of the $^{212}$Pb-labeled antibody component in the $^{224}$Ra solution was verified as in example 8. Animal experiments were performed according to European regulations for animals used for scientific purposes. Animals were euthanized and blood drawn from the heart before they were dissected. Urine, blood and tissue samples were placed in 5 ml tubes. The weight of the tubes were measured before and after addition of samples to determine exact sample weight. The radioactivity content were measured in the Cobra gamma counter. Samples were counted shortly after the dissection and again after 3-4 days when radioactive equilibrium had been reached to determine $^{212}$Pb and $^{224}$Ra content, respectively.

Results: The biodistribution profiles are shown in FIG. 3 C. The $^{212}$Pb showed a distribution profile as expected for a radiolabeled antibody, i.e., high activity in blood and blood rich tissues and low activity in femur and scull. Compared with free $^{212}$Pb (FIG. 3 A), the TCMC-trastuzumab (Herceptin) conjugated $^{212}$Pb had significantly less uptake in femur and scull while the activity level in blood and blood rich organs were higher. It should be noted that the quality of the distribution is different in blood for free $^{212}$Pb and $^{212}$Pb-TCMC-herceptin as the latter is circulating with a slow blood clearance but not taken up in the blood cells as with the free $^{212}$Pb. The $^{224}$Ra showed high uptake in femur and scull and low uptake in blood and was very similar to that found in the biodistribution of chelator free radium solution (FIG. 3 A).

In Table 4 the uptake ratios for bone vs blood and bone vs. kidney for $^{212}$Pb, $^{212}$PB-EDTMP and $^{212}$Pb-TCMC-trastuzumab in $^{224}$Ra solutions are presented. The ratios show improved bone to blood and bone to kidney ratios for $^{212}$Pb-EDTMP compared with non-complexed $^{212}$Pb. For $^{212}$Pb-TCMC-herceptin, however, the bone to blood ratios were lower than for free $^{212}$Pb. This is expected since macromolecular sized monoclonal antibodies clear slowly from the blood compared with most small molecular weight compounds. This may be an advantage when targeting circulating tumor cells as the increased residence time in blood enhances the probability of binding to target cells in circulation. It should also be noted that for short radiation range alpha particles the effect of cellular bound radionuclide may be much stronger than that of circulating radionuclide because of the short proximity to the DNA for cell associated-vs. the freely circulating radionuclide.

In conclusion: Chelator labeled monoclonal antibody can effectively scavenge $^{212}$Pb without reducing the bone seeking properties of $^{224}$Ra in radiopharmaceutical solutions containing the two radionuclides. Thus, it shows the possibility of obtaining dual targeting properties of $^{224}$Ra/$^{212}$Pb by adding complexing agents to the solutions, thereby strengthening the therapeutic potential of the radiopharmaceutical solution and reducing possible undesired uptake of $^{212}$Pb in hematopoietic cells and tissues while upholding the bone seeking properties of $^{224}$Ra.

Example 10

A Kit System for Avoiding Radiolysis

Because of the highly localized nature of alpha-irradiation radiolysis must be considered as a potential problem and the radiopharmaceutical must be designed to minimize this. According to the knowledge in the field radiolabeled antibodies are sensitive to radiolysis and therefore a kit system may be advantageous for $^{224}$Ra solutions which are to be combined with chelator conjugated antibodies for scavenging $^{212}$Pb. When $^{224}$Ra is in equilibrium with progenies it produces approximately 28 MeV per decay of the complete series. Thus, a solution of 1 MBq/ml contains N=A/λ=10$^6$ s-1/(0.693/[3.64×24×3600 s])=4.53×10$^{11}$ atoms of $^{224}$Ra where N is the number of atoms and A is activity in Bq and λ is the decays constant which is equal to ln 2/t$_{1/2}$ and t$_{1/2}$ is the half life for $^{224}$Ra.

The radiation dose, D, is defined as energy per mass, i.e., J/kg in SI-units.

For the complete decay of 1 MBq of $^{224}$Ra in 1 ml of aqueous liquid it would amount to D=(4.53×10$^{11}$×28 MeV× 1.6×10$^{-13}$ J/MeV)/10$^{-3}$ kg=2029 Gy that is, in one half life of 3.64 days a solution of 1 MBq/ml of $^{224}$Ra in equilibrium with daughters will be exposes to about 1 kGy of self-irradiation. For a monoclonal antibody it is usually advisable be keep the self dose of the radiopharmaceutical solution below 0.5 kGy to avoid reduced binding properties due to radiolysis.

Thus, a kit system whereby chelator conjugated antibody is added, e.g., by a syringe to a vial containing the $^{224}$Ra (including daughters) solution a few hours to a few minutes before the product is administered to a patient is advised for concentrated solutions of $^{224}$Ra with progenies suitable for long distance shipment.

Example of scavenging $^{212}$Pb with TCMC-monoclonal antibody conjugate in a 7 days old $^{224}$Ra solution. A $^{224}$Ra solution produced one week earlier was added 10% ammonium acetate and TCMC-rituximab (to a final concentration of about 5 mg/ml) to a final volume and pH of about 0.1 ml and 5.5, respectively, and kept at room temperature overnight. After 18 hours a sample was withdrawn and mixed with formulation buffer as described. TLC analyses showed that 91% of the $^{212}$Pb activity was protein bound, i.e., in the lower half of the TLC strip as determined by gamma counting. This demonstrates that a kit with a vial containing a $^{224}$Ra solution and a separate vial with a chelator-labeled protein or similar can be combined and used to scavenge $^{212}$Pb in the $^{224}$Ra several days after $^{224}$Ra production date, thereby preparing a $^{224}$Ra bone-seeker with a $^{212}$Pb tumor-seeking complex using short reaction times to avoid radiolytic degradation of the product.

It was verified that the reagents, other than $^{224}$Ra, could be stored several weeks or months without losing their function, thus, they are well suited for use in a kit format.

Example 11

Circulating Tumor Cells

Circulating tumor cells could give rise to new tumor lesions in bone or soft tissues and may be addressed by the novel radiopharmaceutical solution described herein.

One may argue that the amount of $^{212}$Pb in therapeutic $^{224}$Ra solution may be moderate to modest (i.e., at equilibrium about 1.1 times that of $^{224}$Ra). If one assume similar dosing of $^{224}$Ra as is done with $^{223}$Ra in patients but correct for the half life difference, roughly 150 kBq per kg of bodyweight would be the administered dose. This is just an example and a dosing may differ significantly according to disease and what level of side effects that is acceptable.

At equilibrium 150 kBq per kg of body weight would translate into a $^{212}$Pb-antibody conjugate dosage of about 11.5 MBq in 5 liter of blood in a 70 kg patient. The number of circulating tumor cells is typically less that 10 cells per ml thus in 5 l blood there are less than 50 000 tumor cells in total. If only 1 in 100 000 of the injected $^{212}$Pb-antibody conjugate binds to the tumors cells this would mean 0.0023 Bq per cell, equivalent to 127 $^{212}$Pb atoms bound per cell, which would be highly destructive as it has been reported that a mean of 25 cell bound $^{212}$Pb per cell would kill 90% of a cell population.

The number of atoms bound to a cell will depend on the specific activity of the $^{212}$Pb-conjugated antibody and the number of antigens available at the target cells. Lead-212 labeled TCMC-trastuzumab with a specific activity of about 37 MBq/mg (1 mCi/mg) was recently evaluated in a clinical study.

A $^{212}$Pb-labeled monoclonal antibody with a specific activity of 37 MBq per mg has a $^{212}$Pb atom to antibody molecule radio of 1:1973, that is, very few of the antibody molecules are actually radiolabeled. To reach a 90% cell kill level of $^{212}$Pb of 25 atoms per cell, one would need to bind 49325 antibody molecules per cell. This is obtainable as several tumor associated antigens are expressed at levels exceeding this. Also from a chemical stand point this is plausible as it is possible to conjugate typically 1 to 5 chelator units per antibody molecule without losing the antigen binding properties, so a very small fraction of the chelator-groups are actually occupied by $^{212}$Pb during and after the radiolabeling.

REFERENCES

Jaggi J S, Kappel B J, McDevitt M R, Sgouros G, Flombaum C D, Cabassa C, Scheinberg D A. Efforts to control the errant products of a targeted in vivo generator. Cancer Res. 2005 Jun. 1; 65(11):4888-95.

Jones S B, Tiffany L J, Garmestani K, Gansow O A, Kozak R W. Evaluation of dithiol chelating agents as potential adjuvants for anti-IL-2 receptor lead or bismuth alpha radioimmunotherapy. Nucl Med Biol. 1996 February; 23(2):105-13.

Nilsson S, Larsen R H, Fosså S D, Balteskard L, Borch K W, Westlin J E, Salberg G, Bruland O S. First clinical experience with alpha-emitting radium-223 in the treatment of skeletal metastases. Clin Cancer Res. 2005 Jun. 15; 11(12):4451-9.

What is claimed is:

1. A radiopharmaceutical solution comprising a free uncomplexed $^{224}$Ra in solution with $^{212}$Pb complexed with EDTMP, antibody-conjugated-DOTA, or antibody-conjugated-TCMC.

2. The radiopharmaceutical solution according to claim 1, wherein $^{212}$Pb is complexed with a TCMC-conjugated monoclonal antibody.

3. A method of making a radiopharmaceutical solution of claim 1 comprising:
mixing a solution comprising free uncomplexed $^{224}$Ra and $^{212}$Pb complexed with EDTMP, antibody-conjugated-DOTA, or antibody-conjugated-TCMC.

4. A method of treating a skeletal disease comprising:
administering the radiopharmaceutical solution of claim 1 to a subject that has a skeletal disease wherein the skeletal disease is a skeletal metastases cancer selected from breast, prostate, kidneys, lung, bone, thyroid, multiple myeloma, primary skeletal, or osteosarcoma.

5. The radiopharmaceutical solution according to claim 1, wherein $^{212}$Pb is complexed with EDTMP.

6. The radiopharmaceutical solution according to claim 1, wherein $^{212}$Pb is complexed with a DOTA-conjugated monoclonal antibody.

7. The radiopharmaceutical solution according to claim 1, wherein the complexing agent is (Herceptin) TCMC-trastuzumab.

8. The radiopharmaceutical solution according to claim 1, wherein the solution is in a volume of 100 μL to 10 mL and the radioactivity is 100 kBq to 100 MBq.

* * * * *